(12) United States Patent
Gupta

(10) Patent No.: US 6,375,804 B1
(45) Date of Patent: Apr. 23, 2002

(54) TERTIARY BUTYL ACETATE RECOVERY

(75) Inventor: Vijai P. Gupta, Berwyn, PA (US)

(73) Assignee: ARCO Chemical Technology, L.P., Greenville, DE (US)

(*) Notice: Subject to any disclaimer, the term of this patent is extended or adjusted under 35 U.S.C. 154(b) by 0 days.

(21) Appl. No.: 09/829,502

(22) Filed: Apr. 10, 2001

(51) Int. Cl.[7] .............................. B01D 3/38; B01D 3/42; C07C 67/54

(52) U.S. Cl. .................. 203/1; 203/3; 203/14; 203/92; 203/96; 203/2; 203/DIG. 21; 560/248; 562/608

(58) Field of Search .............................. 203/2, 3, 14, 16, 203/92, DIG. 21, 96; 560/218, 248; 562/608

(56) References Cited

U.S. PATENT DOCUMENTS 4,204,915 A * 5/1980 Kurata et al. .................. 203/2
4,314,947 A * 2/1982 Hohenschutz et al. ...... 560/248
5,980,696 A * 11/1999 Parten et al. .................. 203/1
5,994,578 A 11/1999 Karas ........................ 560/247

FOREIGN PATENT DOCUMENTS

CS 233464 * 3/1985
RO 106989 * 8/1993

* cited by examiner

Primary Examiner—Virginia Manoharan
(74) Attorney, Agent, or Firm—William C. Long

(57) ABSTRACT

The present invention provides a distillation separation method whereby tertiary butyl acetate is separated by distillation as an overhead stream from a bottoms acetic acid stream with the proviso that water is incorporated in the system such that the bottoms acetic acid stream contains water in amount of 0.1 to 5 wt %.

3 Claims, 1 Drawing Sheet

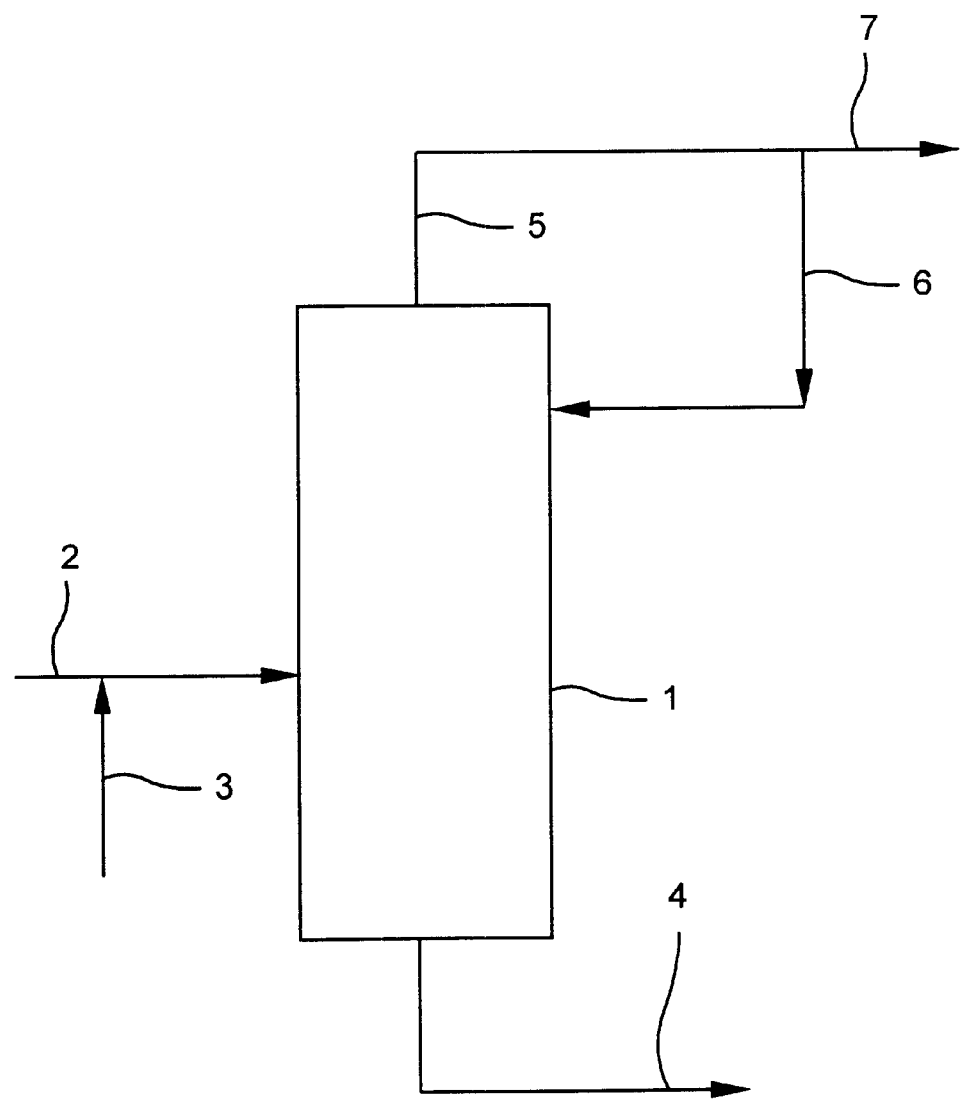

TERTIARY BUTYL ACETATE RECOVERY

BACKGROUND OF THE INVENTION

1. Field of the Invention

The present invention relates to the separation of tertiary butyl acetate from associated acetic acid by a distillation process wherein a substantial concentration of water is maintained in the acetic acid distillation bottoms stream thus enhancing purity of the separated tertiary butyl acetate while suppressing corrosion in the distillation column.

2. The Prior Art

Tertiary butyl acetate is chemical of commerce which is rapidly growing in sales volume and importance.

Although a number of methods are known for production of tertiary butyl acetate an especially advantageous procedure involves the catalytic reaction of isobutylene and acetic acid. See, for example, U.S. Pat. No. 5,994,578. Other processes involve reaction of acetic anhydride with tertiary butanol, and the like.

In such processes, product tertiary butyl acetate is associated with acetic acid and must be separated from the acetic acid prior to use. Frequently product mixtures also contain other impurities such as tertiary butanol, isobutylene oligomers, and the like which also must be separated.

A particular problem encountered in the distillation separation of tertiary butyl acetate and acetic acid is that under normal conditions the acetic acid is quite corrosive.

Production of t-butyl acetate is generally carried out by reacting acetic acid with isobutylene, or acetic anhydride with t-butanol, or a combination of these reactions. The reaction product in all cases contains free acetic acid along with the other reactants and reaction products and by-products such as di- and tri-isobutylene. To recover pure t-butyl acetate, the unreacted acetic acid must be separated from the reaction mass and generally recycled to the reactor.

Acetic acid being the heavy species in the reaction mass, is separated as a distillation column bottoms, while the other components are taken over as a distillate. Concentrated, boiling acetic acid generally corrodes commonly used stainless steels (304, 316) at a rate generally unacceptable for the life of the equipment. Metals from corrosion carried by the acetic acid as a recycle stream, are picked up by the ion exchange resin, if used as catalyst, reducing its life. It is thus, very desirable to reduce corrosion by acetic acid in the distillation column separating the acid.

Separation of acetic acid from the mixture containing t-butyl acetate, t-butanol, and isobutylene and its oligomers is also difficult. To reduce acetic acid to less than 100 ppm level in the distillate requires a large number of separation stages and high reflux, leading to low productivity. It is very desirable to improve this separation step.

SUMMARY OF THE INVENTION

In accordance with the invention, tertiary butyl acetate and acetic acid are separated by distillation; the distillation conditions are regulated to provide a concentration of water in the distillation column bottoms in the range of 0.1 to 5 wt %, preferably 0.3 to 0.7 wt %, to suppress corrosion, and to maintain a concentration of water in the upper part of the column to enhance the separation of acetic acid from the other components.

BRIEF DESCRIPTION OF THE DRAWINGS

The accompanying drawing illustrates schemicatically practice of the invention.

DETAILED DESCRIPTION

Distillation column 1 is provided which is of a conventional structure. The column may be a packed column or a-multi-tray column, for example. The stream comprised of both tertiary butyl acetate and acetic acid is fed via line 2 into the distillation column. Generally speaking, the relative amounts of tertiary butyl acetate and acetic acid in this feed stream range from about 5 to 50 wt % tertiary butyl acetate and 20 to 85 wt % acetic acid. Introduced at the point of introduction of the mixed tertiary butyl acetate and acetic acid feed stream or below that point is a stream comprised of water which is introduced via line 3. Water is introduced preferably at or below the introduction point of the mixed stream to be separated and sufficient water is added so as to maintain the appropriate concentration of water throughout the column.

In distillation column 1 a distillation separation of tertiary butyl acetate and acetic acid is carried out with a bottoms stream comprised of acetic acid separated via line 4. An essential feature of the process of the present invention is that conditions are controlled in column 1 such that the water content of the bottoms acetic acid stream must be maintained in the range of about 0.1 to 5 wt % water, preferably about 0.3 to 0.7 wt % water. An overhead stream is separated via line 5 and comprises a tertiary butyl acetate stream having a significantly reduced content of acetic acid; preferably less than 0.1 wt %.

The feed stream introduced via line 2 can contain, in addition to the tertiary butyl acetate and acetic acid, substantial amounts of other materials such as tertiary butyl alcohol, and various ethers and oligomers associated with the production of tertiary butyl acetate, such as by the reaction of isobutylene with acetic acid. An outstanding feature of the present invention is that the introduction of water via line 3 aids in the separation of acetic acid from both tertiary butyl acetate and the other impurities, the latter being removed in the overhead stream via line 5 from the bottoms acetic acid stream. In addition column corrosion is greatly reduced.

Conditions of operation of column 1 generally involve maintaining the overhead temperature in the range of about 40 to 110° C. and the overhead pressure at about 4 psia to 25 psia. Bottoms conditions generally involve the maintenance of temperatures in the range of about 80 to 135° C. and pressures in the range of about 4 psia to 25 psia. Conveniently, heat is provided to column 1 by means of a conventional reboiler (not shown).

The control of the composition of the bottoms stream removed via line 4 to maintain therein the above described water content enables the successful separation of tertiary butyl acetate and acetic acid while minimizing corrosion. Contrary to prior practices, the separation of acetic acid from the tertiary butyl acetate is essentially complete as a result of the provision of water addition to the distillation column.

Tertiary butyl acetate removed overhead via line 5 can conveniently be separated from the other impurities associated therewith by conventional procedures.

Generally the overhead can be divided into a net product stream removed via line 7 after condensation, and a reflux stream returned to column 1 via line 6 with or without decantation.

Thus, practice of the present invention provides a straight forward and attractive method for recovering tertiary butyl acetate in high purity with minimal corrosion and reduced energy consumption from admixture from acetic acid such as results from a process for the preparation of tertiary butyl acetate by a reaction of isobutylene and acetic acid as described, for example, in U.S. Pat. No. 5,994,578.

The following example is intended to illustrate practice of the present invention.

Referring to the attached FIG. 1, distillation column 1 represents a packed column having 40 theoretical stages. A stream comprised by weight of 25% tertiary butyl acetate, 67% acetic acid, and 8% tertiary butanol is introduced via line 2 at the rate of 10,000 lbs/hr at about the 20th therorectical stage in the column. Also introduced via line 3 with the mixed tertiary butyl acetate and acetic acid stream is a stream comprised of water in amount of 466 lbs/hr. Heat is provided to the column by reboiler means (not shown) and conditions are maintained such that the acetic acid bottoms stream removed via line 4 is removed at 115° C. The column is operated at atmospheric pressure and a reflux ratio of 1.4. The bottoms stream comprises by weight 93% acetic acid, 6.3% t-butanol, 0.1% t-butyl acetate, and 0.5% water and is removed via line 4 at the rate of 7,200 lbs/hr.

An overhead stream is removed via line 5, this stream has the composition of 76.3 wt % tertiary butyl acetate, 13.2 wt % water 10.5 wt % tertiary butanol. A net product is recovered via line 7 at the rate of 3,266 lbs/hr. A portion is returned to column 1 without separation via line 6 at a rate of 4,445 lbs/hr.

The iron content of the bottoms stream was unmeasurable, being below 1 ppm indicating an absence of significant corrosion in the stainless steel column.

From the results of the forgoing, it can be seen that the present invention provides a convenient and economical method for separating from tertiary butyl acetate the normally difficultly separable acetic acid which is associated with tertiary butyl acetate in most methods of manufacture. The removed aqueous acetic acid stream can be further treated to recover acetic acid for recycle to the tertiary butyl acetate production procedure. The overhead stream comprised of tertiary butyl acetate essentially free of acetic acid can be treated in accordance with conventional procedures to produce a commercial quality tertiary butyl acetate product.

COMPARATIVE EXAMPLE

The following example shows operation of the same column under comparable conditions but without the addition of water to the feed stream:

Referring to the attached FIG. 1, distillation column 1 represents a packed column of 316 stainless steel construction and having 40 theoretical stages. A stream comprised by weight of 25% tertiary butyl acetate, 67% acetic acid and 8% tertiary butanol is introduced via line 2 at the rate of 10,000 lb/hr at about the 20th theoretical stage in the column. No water is introduced via line 3. Heat is provided to the column by means of a reboiler (not shown) and conditions are maintained such that the bottoms stream removed via line 4 is removed at 115° C. The column is operated at atmospheric pressure and at a reflux ratio of 4.4. The bottoms stream comprises by weight 95% acetic acid, 4.8% tertiary butanol, 0.1% tertiary butyl acetate and no water, is removed at a rate of 7,049 lb/hr. The iron content in the column bottoms stream ranges between 4–6 ppm, indicating corrosion at an unacceptable rate.

An overhead stream comprised of 84.5% tertiary butyl acetate, 15.5% tertiary butanol and 25 ppm acetic acid is removed via line 5. Net product is recovered via line 7 at a rate of 2,951 lb/hr. Reflux is returned via line 6 at a rate of 13,146 lb/hr.

The above two examples demonstrate that with the addition of a small amount of water to the feed to the distillation column, acetic acid is completely removed from the tertiary butyl acetate rich stream, and the column is protected from corrosion.

I claim:

1. In a process for the separation of tertiary butyl acetate and acetic acid wherein a mixture comprised of tertiary butyl acetate and acetic acid is introduced into a fractional distillation column and separated by fractional distillation, the improvement which comprises introducing water into the distillation column at or below the point of introduction of the tertiary butyl acetate and acetic acid mixture, distilling the mixture and separating a tertiary butyl acetate stream overhead and an acetic acid stream bottoms stream, the distillation conditions being controlled to maintain a water content in the bottoms acetic acid stream of 0.1 to 5 wt. %.

2. A The process of claim 1 wherein the bottoms stream contains 0.3 to 0.7 wt % water.

3. The process of claim 1 wherein the distillation conditions are controlled to provide an overhead temperature of about 40 to 110° C., an overhead pressure of about 4 psia to 25 psia, a bottoms temperature of about 80 to 135° C. and a bottoms pressure of about 4 to 25 psia.

* * * * *